United States Patent [19]

Meissner

[11] Patent Number: 5,050,982

[45] Date of Patent: Sep. 24, 1991

[54] METHOD AND APPARATUS FOR IMPROVING VISUAL ACUITY

[76] Inventor: Juergen P. Meissner, 551 Rte. 10, Randolph, N.J. 07869

[21] Appl. No.: 418,387

[22] Filed: Oct. 6, 1989

[51] Int. Cl.$^5$ .............................................. A61B 3/00
[52] U.S. Cl. ..................................... 351/203; 351/45
[58] Field of Search .................. 351/202, 203, 158, 45, 351/46

[56] References Cited

U.S. PATENT DOCUMENTS

| | | |
|---|---|---|
| 709,058 | 9/1902 | Stierle . |
| 742,081 | 10/1903 | Stierle . |
| 1,313,262 | 8/1919 | Compere . |
| 1,637,406 | 8/1927 | Brumder . |
| 1,844,232 | 2/1932 | Tharp . |
| 1,905,415 | 4/1933 | Lemel . |
| 1,982,650 | 12/1934 | Fletcher . |
| 1,985,668 | 12/1934 | Peavey . |
| 2,057,066 | 10/1936 | Smith . |
| 2,406,190 | 8/1946 | Burdick . |
| 2,475,522 | 7/1949 | Scherkenbach . |
| 2,897,816 | 8/1959 | Williams . |
| 3,268,228 | 8/1966 | Novack . |
| 3,421,233 | 1/1969 | Gaal . |
| 3,498,293 | 3/1970 | Oppenheimer . |
| 3,555,563 | 1/1971 | Grossman . |
| 4,023,892 | 5/1977 | Smith . |
| 4,049,339 | 9/1977 | Ledan . |
| 4,168,111 | 9/1979 | Baines . |
| 4,253,745 | 3/1981 | Bizzarri . |
| 4,464,027 | 8/1984 | Cooper . |
| 4,498,743 | 2/1985 | Feinbloom . |
| 4,531,743 | 7/1985 | Lott . |
| 4,582,401 | 4/1986 | Grindle . |
| 4,602,856 | 7/1986 | Marks . |
| 4,790,643 | 12/1988 | Grandiere . |

FOREIGN PATENT DOCUMENTS 506577 9/1930 Fed. Rep. of Germany .

OTHER PUBLICATIONS

"The Automatic Occluder, A New Concept", Journal of the American Optometric Association, by Merrill J. Allen, vol. 47, No. 7, Jul. 1976.
Adler's Physiology of the Eye by Robert A. Moses, Chapter 23, "Binocular Vision", pp. 653–688, The C. V. Mosby Company, St. Louis, 1970.
"Of Two Minds: Selling the Right Brain", Discover, pp. 30–41, Apr., 1985.
"Color Perception—Seeing with the Brain" by Geoffrey Montgomery, Discover, pp. 52–59, Dec. 1988.
"Memory" by Kevin McKean, Discover, pp. 18–27, Nov. 1983.
"The Mind within the Brain" by Gina Maranto, pp. 34–43, Discover, May, 1984.
"Data Transformation Explains the Basics of Neural Networks" by Doug Conner, EDN, May 12, 1988, pp. 138–144.
"The Mind in Motion" by Geoffrey Montgomery, Discover, Mar., 1989, pp. 58–68.
"3-D Comes Home" by Tom Waters, Discover, May, 1988, pp. 30–32.

Primary Examiner—Paul M. Dzierzynski
Attorney, Agent, or Firm—Richard M. Goldberg

[57] ABSTRACT

A method and apparatus for improving visual acuity during sports activities includes the steps of increasing the strength of the image on the brain half corresponding to the weaker eye of a person by substantially occluding ambient light to the dominant eye of the person for a period of approximately one to two weeks for at least one hour per day; forcing both brain halves to operate at substantially equal visual levels in coordination with each other by wearing eyeglasses having inner opaque sections adjacent the nose bridge so as to limit overlapping vision of the two eyes to a small overlapping area, the inner opaque areas being inwardly and downwardly inclined at an angle of approximately 20 with respect to a nasal axis extending through the nose of the person; and forcing both brain halves to operate independently of each other at substantially equal visual levels by increasing the areas of the opaque sections so as to eliminate the overlapping area, which forces each brain half to process the visual information supplied to it independently of the other brain half, such that the eyes of the person can operate independently and in synchronism, with the same angle of approximately 20 being maintained.

34 Claims, 2 Drawing Sheets

FIG. 4
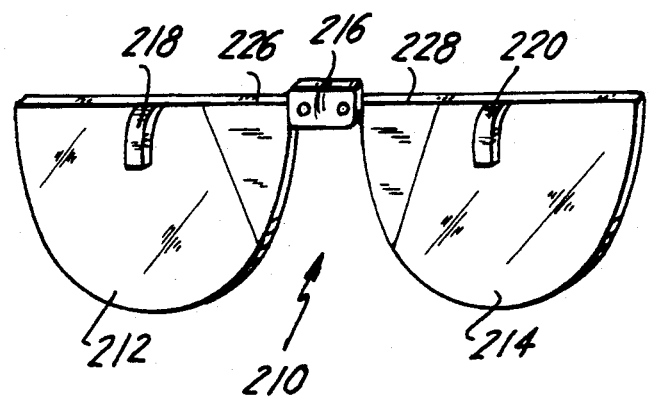
FIG. 5
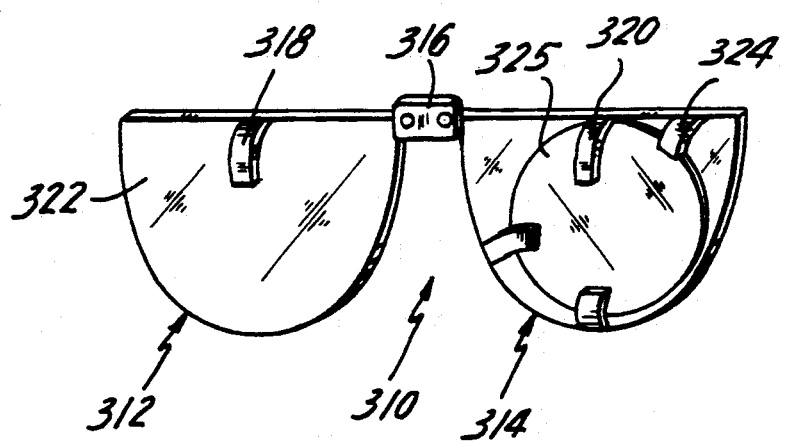
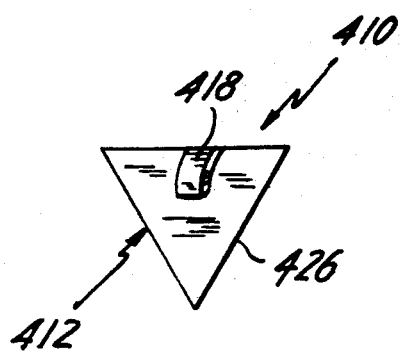
FIG. 6

METHOD AND APPARATUS FOR IMPROVING VISUAL ACUITY

This invention relates generally to a method for improving visual acuity, and more particularly, is directed to a method of improving visual acuity during sports activities.

It is well-known that every person has a weaker or recessive eye. As a result, most people favor the use of one eye (the dominant eye) over the other (the weaker or recessive eye). In such case, only the image from the brain half corresponding to the dominant eye is used. Specifically, although both eyes are operational to view an object, the image the weaker eye has a greatly reduced light intensity compared with the image from the dominant eye. This means that, although the weaker eye aids the brain in interpreting a three-dimensional image, the primary sensory input is to the brain half corresponding to the dominant eye. Therefore, during normal activities, and particularly during sports activities, only the image to one brain half, corresponding to the dominant eye is used, with the image from the weaker eye being used only to aid in determining three-dimensional space.

This, however, is particularly disadvantageous during sports activities. As an example, in the sport of tennis, and assuming that the subject player is right-handed and has a dominant right eye, which is the situation in the majority of cases, for a back-hand return the dominant right eye is used to follow the tennis ball as it approaches. This corresponds to use of only the left brain half. However, once the tennis ball passes the medial line of the face defined by the player's nose, the right eye no longer sees the ball. Accordingly, the left or weaker eye takes over. A problem results because the brain has been trained to use only the image from the brain half corresponding to the right, dominant eye for viewing the object, with the weaker left eye being used only for three-dimensional aiding purposes. In such case, the image from the weaker left eye during such movement of the ball is inhibited by the brain and not used to form the image. In other words, the image on the right brain half corresponding to the left eye is not used. As a result, a blind spot (scotoma) or area results, and the user no longer sees the tennis ball. The reason that the player can hit and return the tennis ball is due to reconstruction by the brain from the flight path visualized by the dominant right eye, which depends upon the trajectory, angle, speed and the like of the tennis ball. This, however, is disadvantageous since it is only a reconstruction, rather than an actual and timely sighting of the tennis ball at the point of impact.

On the other hand, for a forehand return, the right eye continuously watches the tennis ball from the time of its return from the opposite side of the net, to the point of impact. This is why many tennis players find it easier to hit a forehand return than a backhand return, even though the backhand return is a more natural stroke. For those tennis players with a better backhand return than a forehand return, the weaker eye is generally the right eye while the dominant eye is the left eye.

However, with the top-rated tennis players of the world, the left and right eyes operate substantially independently of each other and at substantially equal levels. For example, during a backhand return, the right eye will produce the dominant image for the brain. As soon as the ball passes the medial plane of the player's nose, the left eye becomes the dominant eye for producing the image to the brain so that the tennis player actually sees the ball at the point of impact with the left eye.

Although the above discussion has been given with respect to the sport of tennis, the same problems result in other sports activities, as well as normal, everyday life experiences.

OBJECTS AND SUMMARY OF THE INVENTION

Accordingly, it is an object of the present invention to provide a method for improving dynamic visual acuity.

It is another object of the present invention to provide a method for improving dynamic visual acuity during sports activities.

It is still another object for the present invention to provide a method of strengthening the image from the weaker eye with respect to the image from dominant eye.

It is yet another object of the present invention to provide a method for improving visual acuity during sports activities in which the image from each eye is processed separately by the different brain halves so that either image can be used, depending upon the need at the time.

It is a further object of the present invention to provide such a method in which opposite brain halves are forced to work separately from each other.

In accordance with an aspect of the present invention, a method for improving visual acuity includes the steps of increasing the strength of the image on a brain half corresponding to a weaker eye of a person; forcing both brain halves to operate at substantially equal visual levels in coordination with each other; and then forcing both brain halves to operate independently of each other at substantially equal visual levels.

In accordance with another aspect of the present invention, a method for improving visual acuity, includes the step of forcing both brain halves to operate independently of each other at substantially equal visual levels by substantially occluding ambient light to both eyes in a light restriction area so as to prevent any overlap between images from both eyes of the person, the step of forcing including the step of forming outer edges of the light restriction area on both sides of the nose of the person extending inwardly and downwardly in an inclined manner at an angle in the range of approximately 15 to 25 with respect to a nasal axis extending through the nose of the person, to provide substantially identical areas of viewing for each eye, for both close-up viewing and distance viewing.

In accordance with still another aspect of the present invention, a method for improving visual acuity, includes steps of increasing the strength of the image on a brain half corresponding to a weaker eye of a person; and forcing both brain halves to operate independently of each other at substantially equal visual levels.

In accordance with yet another aspect of the present invention, a method for improving visual acuity, includes the steps of forcing both brain halves to operate at substantially equal visual levels in coordination with each other; and forcing both brain halves to operate independently of each other at substantially equal visual levels.

In accordance with a further aspect of the present invention, apparatus for improving visual acuity, includes an eyeglass frame having a left-frame section and a right-frame section, the left-frame section having an inner area which is substantially occluding to an inner portion of the left eye of a person and the right-frame section having an inner area which is substantially occluding to an inner portion of the right eye of the person, each of the substantially occluding areas having an outer edge which is inclined, when worn, in an inwardly and downwardly manner in the range of approximately 15 to 25 with respect to a nasal axis extending through the nose of the person.

The above and other objects, features and advantages of the present invention will become readily apparent from the following detailed description thereof, which is to be read in connection with the accompanying drawings.

BRIEF DESCRIPTION OF THE DRAWINGS

FIG. 4 is a perspective view of a clip-on frame according to another embodiment of the present invention;

FIG. 5 is a perspective view of a clip-on frame according to another embodiment of the present invention; and FIG. 6 is a perspective view of a clip-on frame according to another embodiment of the present invention.

DETAILED DESCRIPTION OF THE PREFERRED EMBODIMENTS

Figure 1:
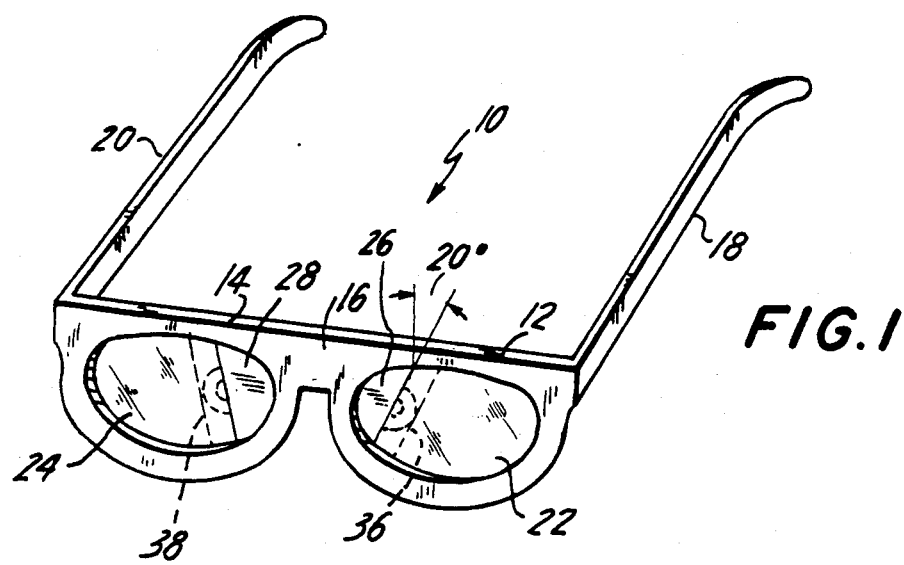
FIG. 1 is a perspective view of a pair of eyeglasses used to perform the method according to one embodiment of the present invention.

As discussed above, every person has a weaker eye. As a result, vision from the weaker eye is inhibited by the brain. In other words, the image from the dominant eye is primarily used to view an object. In such case, only the image from the brain half corresponding to the dominant eye is used. It will be appreciated that this process of using the image from the brain half corresponding to the dominant eye has taken place over the entire lifetime of the person.

In accordance with a first step of the present invention, it is first necessary to increase the strength of the image on the brain half corresponding to the weaker eye so that the images from the weaker eye and dominant eye are substantially equal, or at least that the image on the brain half derived from the weaker eye is greatly increased from its previous level. In this regard, and in accordance with the first step of the present invention, the dominant eye is occluded to prevent an image from forming on the brain half corresponding thereto. This can be accomplished, for example, by means of a patch placed over the dominant eye so that the person is forced to see through the weaker eye. This is a clinically approved method for improving vision for people with an extremely retarded lazy eye, although it is not conventional to use this method with people believed to have normal vision.

During such patching step, bothersome symptoms such as headaches, queasiness, dizziness or the like may appear. It has been found that this step is complete when such bothersome symptoms disappear. In accordance with the present invention, this time period should take a maximum of approximately one to two weeks at a minimum of approximately one hour per day, although wearing such a patch one-half hour per day will help. It has been found that use of such eye patch for periods greater than two weeks becomes redundant and will not further increase the strength of the image from the weaker eye. It has further been found that wearing such a patch every day for short periods of time provides better results than wearing the patch for longer periods of times only a few times per week.

In effect, this step is a brute force step to improve the strength of the image on the brain half corresponding to the weaker eye.

In accordance with the second step of the present invention, with the strength of the image from the brain half corresponding to the weaker eye now increased, both brain halves receive images of substantially equal strength. Ideally, the end result of the present invention will enable both brain halves to operate separately from each other for the same image. For example, during a backhand return in tennis, the right eye would look where the ball came from while the left eye would simultaneously look at the point of contact with the racquet, and the images from the left and right brain halves would switch as controlling, depending upon the location of the tennis ball.

However, the human brain is not accustomed to such independent operation of the two eyes, and accordingly, the ability to do so must be induced through the imposition of an intermediate step in its training. This is accomplished most easily after the brain halves are both operating together and using images of at least nearly equal intensity, as accomplished by the foregoing initial step in the process.

To induce this independent action while eliminating the possibility of the individual brain halves reverting to use of a dominant eye and lazy eye, eyeglasses 10 of FIG. 1 are worn by the user. As shown, eyeglasses 10 are substantially identical to conventional eyeglasses and, in this regard, include left and right lens frames 12 and 14 connected by a nose bridge section 16 and stem members 18 and 20 secured to frames 12 and 14, respectively, for wrapping about the ears of the person to thereby secure eyeglasses 10 on the face of the person. In accordance with the present invention, lens frames 12 and 14 can be provided with corrective lenses 22 and 24, respectively, as is conventional for correcting the vision of the person. In the event that no vision correction is required, or in the event that the person is wearing contact lenses, corrective lenses 22 and 24 would be eliminated, or alternatively, would be replaced by plain, non-corrective glass or plastic lenses.

Figure 2:
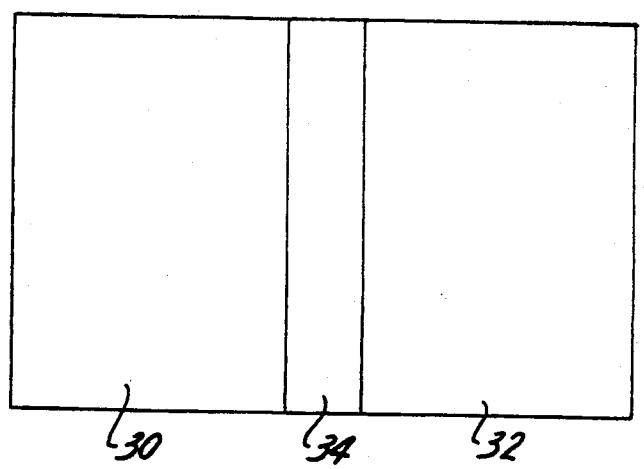
FIG. 2 is an illustrative diagram for describing different areas viewed by the eyes with the pair of eyeglasses of FIG. 1.

In accordance with the present invention, opaque or substantially occluding sections 26 and 28 are positioned over lenses 22 and 24, respectively, adjacent to bridge 16 so as to partially obstruct the vision of the person from both eyes. The meaning of substantially occluding is to provide sufficient blockage of light so that effectively no reasonable image can be used for sight, solely through sections 26 and 28. Initially, as shown in FIG. 2, section 26 restricts the vision from the left eye to an area 30, and section 28 restricts the vision from the right eye to an area 32, with a small central, overlapping area 34 being viewed by both eyes. It will be appreciated that overlapping area 34 is a substantially uniform overlapping area. This is due to the fact that sections 26 and 28 are inclined inwardly and downwardly relative to the vertical medial plane passing through the person's nose. Thus, when the person looks downwardly, for example, during reading, the same overlapping area is substantially provided as when the person is looking at an object far away. In other words, the inclination of sections 26 and 28 permits the person to see objects both near and far with substantially the same overlap. It will be appreciated that although FIG. 2 shows rectangular areas 30, 32 and 34, such areas in reality are not purely rectangular, and are merely shown as such for ease of illustration.

Preferably, the angle of inclination of sections 26 and 28 with respect to a vertical axis 29, as shown in FIG. 1, is in the range of 15-25 degrees with an optimum angle of 20 degrees. Accordingly, the overlapping area 34 remains the same regardless of whether the person is viewing an object at a distance or viewing an object nearby. This is particularly important in training the brain halves, and thereby the eyes, for sports activities since a sports participant often must view an object far away and in a short time period view the same object close by. For example, in the sport of tennis, the tennis player must view the tennis ball on the opposite side of the court, and soon thereafter, at the point of impact on the tennis racket.

With eyeglasses 10, as described above, it will be appreciated that both eyes send substantially equal images to the respective brain halves. Because of the small overlapping area 34, the brain halves are forced to work with each other. As a result, the brain halves are forced to use the images from both eyes substantially equally. The reason for the overlap is to train the two brain halves to accept the two substantially equal images and work with both images, thereby effectively eliminating the weaker eye. In effect, this forces the brain to fuse the two visual images supplied thereto. This is known in the art as "eye-teaming". With eye-teaming, one can see three-dimensional objects more easily, and true stereoscopic vision is enhanced.

In the last step of the present invention, the areas of opaque or substantially occluding sections 26 and 28 are increased, as shown by dashed lines 36 and 38, so as to eliminate overlapping area 34. As a result, each brain half independently and separately analyzes its own image. In this manner, the eyes of the user are forced to move in different directions, when necessary, and each brain half must accept different visual stimuli. For example, during a backhand return in tennis, the right eye looks where the ball came from while the left eye simultaneously looks at the contact point. This is seen in the top-ranked tennis players in the world, in whom, at the time of impact, the eyes of the tennis player are looking in different directions. Of course, it will be appreciated that, although the areas of sections 26 and 28 are increased, the same angle with respect to the vertical axis 29 remains for the same reasons given above. Thus, sections 26 and 28, even when increased in area to lines 36 and 38, are inclined with respect to the vertical axis 29 by the same optimum angle of 20 degrees.

It will be appreciated that the positioning of sections 26 and 28 can be changed to the positions shown by dashed lines 36 and 38, by any suitable means. For example, sections 26 and 28 can be provided by sliding friction plates which slide side-to-side with respect to each frame 12 and 14, and which can be secured in different positions by pins, screws or the like. In like manner, the positioning of sections 26 and 28 can be adjusted to the particular user during the second and/or third steps, in accordance with the inter-pupillary distance of the user.

Figure 3:
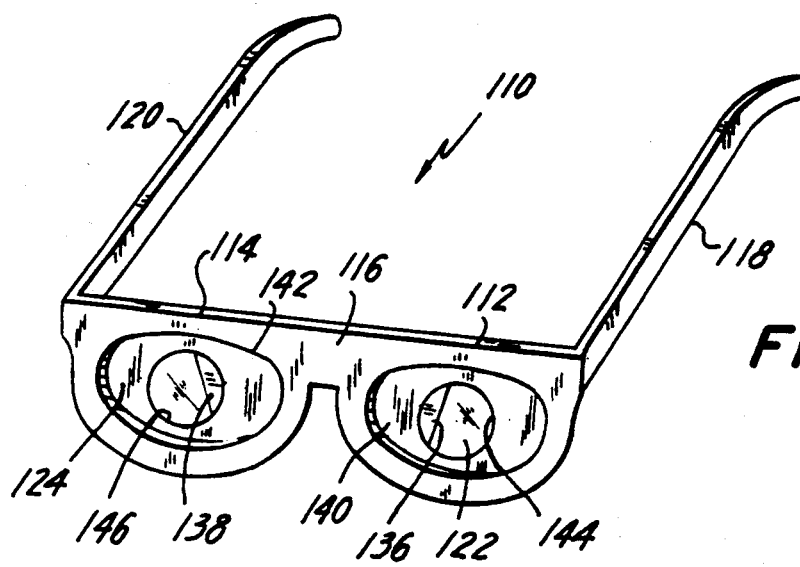
FIG. 3 is a perspective view of a pair of eyeglasses according to another embodiment of the present invention.

Referring now to FIG. 3, eyeglasses 110 according to another embodiment of the present invention, will now be described, in which elements corresponding to those described above with respect to the embodiment of FIG. 1 are identified by the same reference numerals, augmented by 100, and a detailed description thereof will be omitted herein for the sake of brevity.

As shown therein, eyeglasses 110 are identical to eyeglasses 10, with the exception that further opaque or substantially occluding areas 140 and 142 are formed on lenses 122 and 124 so as to form circular viewing areas 144 and 146 which are further reduced by inclined opaque or substantially occluding sections 136 and 138. Sections 136 and 138 perform the same functions as opaque or substantially occluding sections 36 and 38 in the embodiment of FIG. 1.

The reason for forming circular visual areas 144 and 146 is to further restrict the field of vision of the user to a cone of approximately 30 degrees. It has been found herein that, as an athlete tires, is a reduction in field of vision which contracts from approximately 90 degrees at the start of the athletic activity to approximately 30 degrees. Eyeglasses 110, in addition to performing the function of eyeglasses 10, force the person always to restrict his field of vision to such a 30 degrees cone. This forces the person to turn his head and body properly at all times to look at the tennis ball. Then, when the person tires, he has become accustomed to hitting within the 30 degrees cone to which the eyes have been forced, so that there is no change in the level of play.

As an alternative, instead of applying opaque or substantially occluding sections 36, 38, 136 and 138, it is possible to form eyeglasses 10 and 110 with completely opaque or substantially occluding lenses 22, 24, 122 and 124, and then cut out the desired non-restricted areas therefrom.

Although the present invention has been discussed with respect to eyeglasses 10 and 110, it will be appreciated that it can be used with a clip-on frame 210 containing left and right lens frames 212 and 214 connected by a nose-bridge section 216, as shown in FIG. 4. In such case, stem members 18 and 20 of eyeglasses 10 are eliminated and, in place thereof, retaining clips 218 and 220 are secured to the upper portions of left and right lens frames 212 and 214 so as to secure clip-on frame 210 to a conventional pair of eyeglasses normally worn by a person. Of course, it will be appreciated that clip-on frame 210 also includes opaque or substantially occluding sections 226 and 228 which are substantially identical to sections 26 and 28, respectively.

As another alternative, and referring to FIG. 5, in place of the patching step in order to increase the strength of the image on the brain half from the weaker eye, a clip-on frame 310 can be used having frame sections 312 and 314 connected by a nose-bridge section 316, and having retaining clips 318 and 320, respectively secured to the upper ends of frames 312 and 314. Unlike clip-on frame 210 of FIG. 4, clip-on frame 310 does not include any opaque sections 226 and 228. In this case, the lenses 322 and 324 provided with left and right lens frames 312 and 314 are polarized in a single direction. Thus, substantially no light reduction occurs through lenses 322 and 324. However, a second polarizing lens 325 is positioned and secured over one of the lenses, for example, lens 324 in FIG. 5, with its polarizing direction offset with respect to the polarizing direction of lens 324. In this manner, there is a light reduction through one eye, for example, the right eye with the clip-on frame 310 of FIG. 5. The amount of light blockage will depend on the relative rotation between the polarizing directions of lenses 324 and 325. Second polarizing lens 325 is secured to lens 324 by any suitable means, such as an adhesive, or any other suitable means. Second polarizing lens 325 can also be rotatably secured to lens 324 to permit a variable amount of light blockage. As a result, the weaker eye is forced to perform the majority of viewing of the object. However, unlike the patching step previously discussed, the arrangement of FIG. 5 provides the use of both eyes to view the object so as to obtain stereoscopic viewing while still strengthening the image on the brain half from the weaker eye. Thus, the user can perform normal everyday functions.

Alternatively, as shown in FIG. 6, a clip-on frame 410 according to another aspect of the present invention includes a partial frame 412 formed with an opaque or substantially occluding section 426 having a retaining clip 418 secured to the upper portion thereof. Clip-on frame 410 can be secured over the eyeglasses corresponding to the dominant eye of the person. As a result, the person can easily function indoors since there is no tinting as with sunglasses. The key to the patching step is to prevent the dominant eye from looking across the nose of the person to view an object, that is, in order to emphasize use of the image from the weaker eye.

Although the present invention has been discussed for use with tennis, it will be appreciated that the present invention is not limited thereby and can be used with any sporting activity and, in fact, can be used outside of sports activities, that is, in the normal course of everyday life.

Further, although the lens frames have been discussed as being connected by a nose-bridge section, it is possible to construct each lens frame separately, and to connect each lens frame separately from the other, particularly in a clip-on arrangement.

Having described specific preferred embodiments of the invention with reference to the accompanying drawings, it will be appreciated that the present invention is not limited to those precise embodiments, and that various changes and modifications can be effected therein by one of ordinary skill in the art without departing from the spirit or scope of the invention as defined by the appended claims.

What is claimed is:

1. A method for improving visual acuity, comprising the steps of:
    increasing the strength of an image on a brain half corresponding to a weaker eye of a person;
    subsequently forcing both brain halves to operate at substantially equal visual levels in coordination with each other; and
    substantially forcing both brain halves to operate independently of each other at substantially equal visual levels;
    each said step of forcing including the step of substantially occluding ambient light to at least one eye in a light restriction area located in an overlapping viewing area of both eyes.

2. A method according to claim 1, wherein said step of substantially occluding includes the step of forming an outer edge of the light restriction area in an inwardly and downwardly inclined manner with respect to a nasal axis extending through the nose of the person.

3. A method according to claim 2, wherein said outer edge is formed at an angle in the range of approximately 15 to 25 degrees to the nasal axis.

4. A method according to claim 3, wherein said outer edge is formed at an angle of approximately 20 degrees with respect to the nasal axis.

5. A method according to claim 2, wherein said step of substantially occluding includes the step of forming a left light restriction area on the left side of the nose of the person and a right light restriction area on the right side of the nose of the person, each of said left and right light restriction areas having an outer edge extending downwardly and inwardly in an inclined manner with respect to the nasal axis.

6. A method according to claim 2, wherein said step of forcing both brain halves to operate in coordination with each other includes the step of forming said light restriction area with a lesser area than said overlapping viewing area so as to provide some overlapping viewing by both eyes.

7. A method according to claim 2, wherein said step of forcing both brain halves to operate independently includes the step of increasing the size of said light restriction area to be at least equal to said overlapping viewing area so as to eliminate overlapping viewing by both eyes.

8. A method according to claim 2, wherein each said step of forcing includes the step of forming said light restriction area as an opaque area.

9. A method according to claim 2, further including the step of restricting eyesight from each eye to a cone of vision of approximately 30.

10. A method for improving visual acuity, comprising the step of forcing both brain halves to operate independently of each other at substantially equal visual levels by substantially occluding ambient light to both eyes in a light restriction area so as to prevent any overlap between images from both eyes of the person, said step of forcing including the step of forming outer edges of said light restriction area on both sides of the nose of the person extending inwardly and downwardly in a linear inclined manner at an angle in the range of approximately 15 to 25 degrees with respect to a nasal axis extending through the nose of a person, to provide substantially identical areas of viewing for each eye, for close-up viewing, mid-range viewing and distance viewing when the head of the person is still.

11. A method according to claim 10 wherein said outer edge is formed at an angle of approximately 20 degrees with respect to the nasal axis.

12. A method according to claim 10, wherein said step of substantially occluding includes the step of forming a left light restriction area on the left side of the nose of the person and a right light restriction area on the right side of the nose of the person, each of said left and right light restriction areas having an outer edge extending downwardly and inwardly in an inclined manner with respect to the nasal axis.

13. A method according to claim 10, wherein said step of forcing includes the step of forming said light restriction area as an opaque area.

14. A method according to claim 10, further including the step of restricting eyesight from each eye to a cone of vision of approximately 30 degrees.

15. A method for improving visual acuity, comprising the steps of:
    increasing the strength of an image on a brain half corresponding to a weaker eye of a person; and subsequently forcing both brain halves to operate independently of each other at substantially equal visual levels, said step of forcing including the step of substantially occluding ambient light to both eyes in a light restriction area so as to prevent any overlap between images from both eyes of the person.

16. A method according to claim 15 wherein said step of substantially occluding includes the step of forming an outer edge of the light restriction area in an inwardly and downwardly inclined manner with respect to a nasal axis extending through the nose of the person.

17. A method according to claim 16, wherein said outer edge is formed at an angle in the range of approximately 15 to 25 degrees with respect to the nasal axis.

18. A method according to claim 16, wherein said outer edge is formed at an angle of approximately 20 degrees with respect to the nasal axis.

19. A method according to claim 16, wherein said step of substantially occluding includes the step of forming a left light restriction area on the left side of the nose of the person and a right light restriction area on the right side of the nose of the person, each of said left and right light restriction areas having an outer edge extending downwardly and inwardly in an inclined manner with respect to the nasal axis.

20. A method according to claim 16, wherein said step of forcing includes the step of forming said light restriction area as an opaque area.

21. A method according to claim 16, further including the step of restricting eyesight from each eye to a cone of vision of approximately 30.

22. A method for improving visual acuity, comprising the steps of:
forcing both brain halves to operate at substantially equal visual levels in coordination with each other; and
subsequently forcing both brain halves to operate independently of each other at substantially equal visual levels;
each said step of forcing including the step of substantially occluding ambient light to at least one eye in a light restriction area located in an overlapping viewing area of both eyes, said step of substantially occluding including the step of forming an outer edge of the light restriction area in an inwardly and downwardly inclined manner with respect to a nasal axis extending through the nose of the person, said outer edge being formed at an angle in the range of approximately 15 to 25 degrees with respect to the nasal axis.

23. A method according to claim 22, wherein said outer edge is formed at an angle of approximately 20 degrees with respect to the nasal axis.

24. A method for improving visual acuity, comprising the steps of:
forcing both brain halves to operate at substantially equal visual levels in coordination with each other; and
subsequently forcing both brain halves to operate independently of each other at substantially equal visual levels;
each said step of forcing including the step of substantially occluding ambient light to at least one eye in a light restriction area located in an overlapping view area of both eyes, said step of substantially occluding including the steps of forming an outer edge of the light restriction area in an inwardly and downwardly inclined manner with respect to a nasal axis extending through the nose of the person, and forming a left light restriction area on the left side of the nose of the person and a right light restriction area on the right side of the nose of the person, each of said left and right light restriction areas having an outer edge extending downwardly and inwardly in an inclined manner with respect to the nasal axis.

25. A method for improving visual acuity, comprising the steps of:
forcing both brain halves to operate at substantially equal visual levels in coordination with each other;
subsequently forcing both brain halves to operate independently of each other at substantially equal visual levels;
each said step of forcing including the step of substantially occluding ambient light to at least one eye in a light restriction area located in an overlapping viewing area of both eyes, said step of substantially occluding including the step of forming an outer edge of the light restriction area in an inwardly and downwardly inclined manner with respect to a nasal axis extending through the nose of the person; and
said step of forcing both brain halves to operate in coordination with each other includes the step of forming said light restriction area with a lesser area than said overlapping viewing area so as to provide some overlapping viewing by both eyes.

26. A method for improving visual acuity, comprising the steps of:
forcing both brain halves to operate at substantially equal visual levels in coordination with each other;
subsequently forcing both brain halves to operate independently of each other at substantially equal visual levels;
each said step of forcing including the sep of substantially occluding ambient light to at least one eye in a light restriction area located in an overlapping viewing area of both eyes, said step of substantially occluding including the step of forming an outer edge of the light restriction area in an inwardly and downwardly inclined manner with respect to a nasal axis extending through the nose of the person; and
said step of forcing both brain halves to operate independently includes the step of increasing the size of said light restriction area to be at least equal to said overlapping viewing area so as to eliminate overlapping viewing by both eyes.

27. A method for improving visual acuity, comprising the steps of:
forcing both brain halves to operate at substantially equal visual levels in coordination with each other; and
subsequently forcing both brain halves to operate independently of each other at substantially equal visual levels;
each said step of forcing including the step of substantially occluding ambient light to at least one eye in a light restriction area located in an overlapping viewing area of both eyes, said step of substantially occluding including the step of forcing an outer edge of the light restriction area in an inwardly and downwardly inclined manner with respect to a nasal axis extending through the nose of the person;

each said step of forcing including the step of forming said light restriction area as an opaque area.

28. A method for improving visual acuity, comprising the steps of:
forcing both brain halves to operate at substantially equal visual levels in coordination with each other;
subsequently forcing both brain halves to operate independently of each other at substantially equal visual levels;
each said step of forcing including the step of substantially occluding ambient light to at least one eye in a light restriction area located in an overlapping viewing area of both eyes, said step of substantially occluding including the step of forming an outer edge of the light restriction area in an inwardly and downwardly inclined manner with respect to a nasal axis extending through the nose of the person; and
restricting eyesight from each eye to a cone of vision of approximately 30 degrees.

29. Apparatus for improving visual acuity, comprising an eyeglass frame having a left-frame section and a right-frame section, said left-frame section having an inner area which is substantially occluding to an inner portion of the left eye of a person and said right-frame section having an inner area which is substantially occluding to an inner portion of the right eye of the person, each of said substantially occluding areas having an outer edge which is inclined, when worn, in an inwardly and downwardly linear manner in the range of approximately 15 to 25 degrees with respect to a nasal axis extending through the nose of the person, and said substantially occluding areas being of at least an equal area as an overlapping viewing area of both eyes to eliminate overlapping viewing by both eyes so as to force both brain halves to operate independently of each other, and to provide substantially identical areas of viewing for each eye, for close-up viewing, mid-range viewing and distance viewing when the head of the person is still.

30. Apparatus according to claim 29, wherein said left-frame section and said right-frame section are connected together by a nose-bridge section, said inner areas of said left-frame section and said right-frame section being adjacent said nose-bridge section.

31. Apparatus according to claim 30, wherein said eyeglass frame further includes a left stem portion secured to said left-frame section and adapted to be removably secured to the left ear of the person and a right stem portion secured to said right-frame section and adapted to be removably secured to the right ear of the person.

32. Apparatus according to claim 29, wherein each of said left-frame and right-frame sections include a retaining clip for securing said left-frame and right-frame sections on a pair of eyeglasses.

33. Apparatus according to claim 32, wherein said left-frame section and said right-frame section are connected together by a nose-bridge section, said inner areas of said left-frame section and said right-frame section being adjacent said nose-bridge section.

34. Apparatus according to claim 29, wherein said outer edge of each substantially occluding area is formed at an angle of approximately 20 degrees with respect to the nasal axis.

* * * * *